United States Patent [19]

Lunquist

[11] 4,012,103
[45] Mar. 15, 1977

[54] ANTISHOCK, INSULATED CONNECTOR

[75] Inventor: Frank C. Lunquist, New Brighton, Minn.

[73] Assignee: Medtronic, Inc., Minneapolis, Minn.

[22] Filed: Sept. 3, 1975

[21] Appl. No.: 610,068

[52] U.S. Cl. .......................... 339/111; 128/419 P; 200/51.09
[51] Int. Cl.$^2$ ........................................ H01R 13/52
[58] Field of Search ......... 128/419 P, 419 PG, 404; 200/DIG. 2, 51.09, 159 B; 339/111, 177 R, 177 E

[56] References Cited

UNITED STATES PATENTS

| | | | |
|---|---|---|---|
| 2,728,823 | 12/1955 | Auth | 200/51.09 |
| 2,877,324 | 3/1959 | Oshry | 200/159 B |
| 3,284,755 | 11/1966 | Mummey | 339/128 |
| 3,732,390 | 5/1973 | Novak | 200/159 B |
| 3,744,007 | 7/1973 | Horak | 339/177 E |
| 3,908,668 | 9/1975 | Bolduc | 128/419 P |

*Primary Examiner*—Roy Lake
*Assistant Examiner*—Mark S. Bicks
*Attorney, Agent, or Firm*—Cameron, Kerkam, Sutton, Stowell & Stowell

[57] ABSTRACT

An antishock, insulated connector of the type adapted to be electrically coupled to a heart pulse generator is disclosed as comprising an electrically conductive lead coupled to a pin, and a layer of insulating material disposed about the lead and the pin. A further, electrically conductive element is disposed about the insulating layer in an electrically isolated position with respect to the pin and is adapted upon insertion into a female receptacle to be brought into electrical contact with the pin, whereby a circuit is completed through the electrically conductive element, the pin and the lead. In one illustrative embodiment the electrically conductive element comprises a tube-like metallic ring spaced from the pin by a pair of spacers made of an electrically insulating, elastic material and disposed between the pin and the ring, whereby upon application of an offsetting pressure to the metallic ring, the metallic ring is directed toward the pin and the elastic material is compressed so that electrical contact is made between the ring and the pin. In a further embodiment of this invention, the electrically conductive element takes the form of an electrically conductive reed-like member suspended at one end with the other end embedded in an elastomer to be flexed into electrical contact with its electrically conductive pin.

12 Claims, 13 Drawing Figures

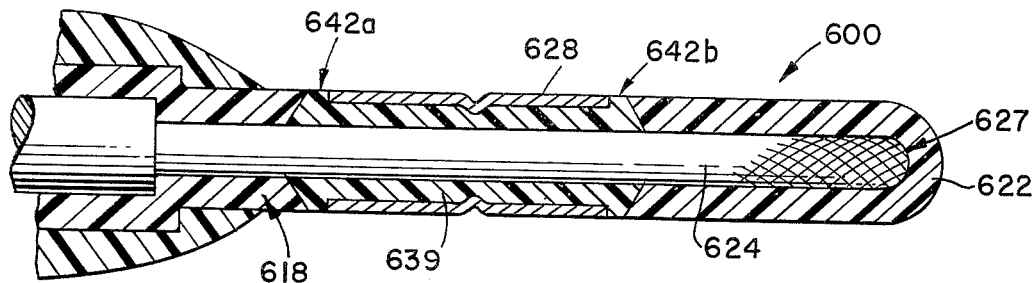
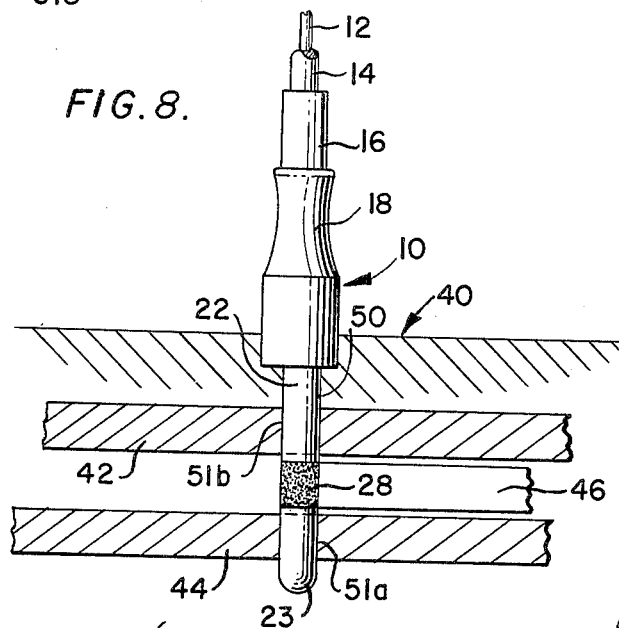
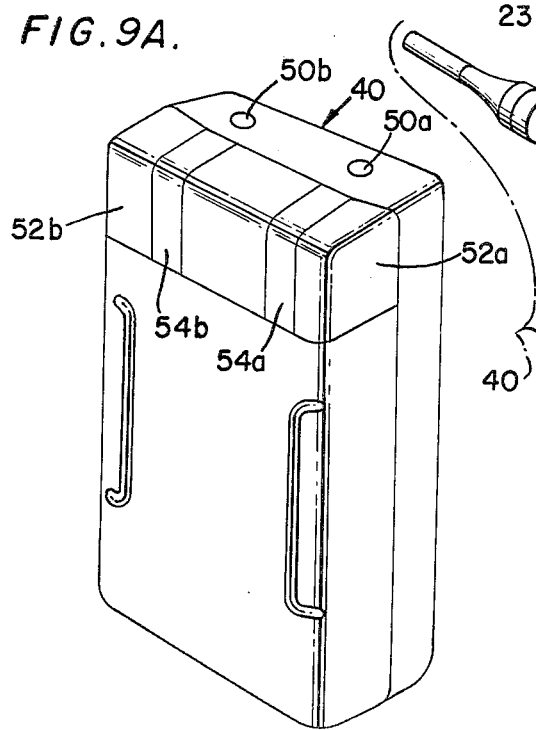
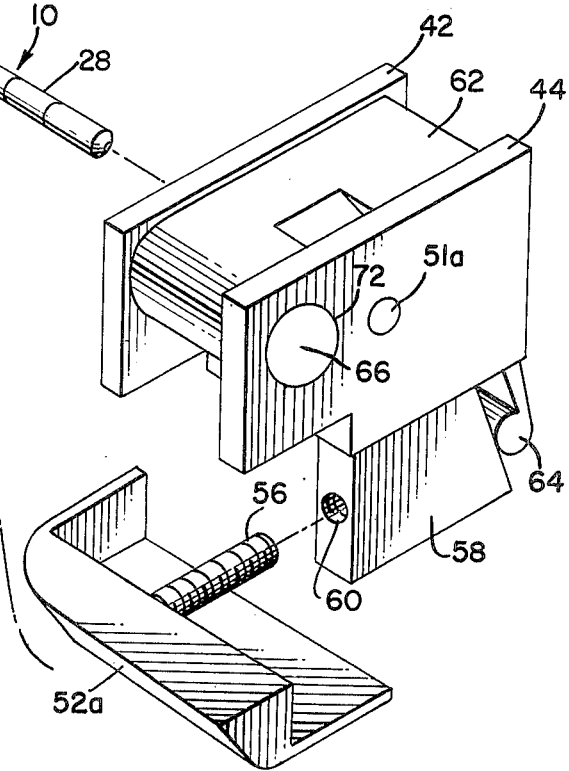

ANTISHOCK, INSULATED CONNECTOR

BACKGROUND OF THE INVENTION

1. Field of the Invention

This invention relates to the field of medical electronics and particularly to an insulated electrode adapted to be coupled to a heart pulse generator in a manner to prevent extraneous signals from being applied through the insulated connector to the patient's heart.

2. State of the Prior Art

Electric stimulation of body tissue and organs is a method of treating various pathological conditions which is becoming quite commonplace. Such stimulation generally calls for making some type of electrical contact with the body tissue or organ. In particular, with respect to the heart, electrical leads are physically coupled or implanted into the myocardial or endocardial tissues.

In order to attach the connectors or electrodes of the heart pulse generator to the heart, it is necessary to make an incision in the neck whereby the leads of an external or implanted pulse generator may be passed through the patient's subclavian vein into the patient's heart. The external pulse generator is for temporary use only and is attached external to the patient's body. The implanted pulse generator and its related lead are fully implanted on a permanent basis within the patient's body. Typically, during such a surgical procedure, the proximal connector, adapted to be electrically attached to the heart pulse generator, remains outside the patient's body, whereby it may inadvertently be exposed to micro-shock energies by contact with one of the participants in the surgical procedure or with some piece of electrically active surgical equipment. In such case, a relatively small energy level in the order of micro-watts would be applied directly to the patient's heart with the possibility that the patient's heart would be driven into fibrillation. If the proximal connector of the pacemaker lead is not effectively isolated from its environment, the possible resultant microshock may be fatal to the patient.

Male-type connectors have typically been used as the proximal connectors for a heart pacemaker system and are particularly adapted for insertion into a female receptacle of the heart pulse generator. However, the shock hazards associated with such male-type connectors has only been recognized in recent years. Presently, the procedures for eliminating such hazards are of a field expedient variety dependent upon the awareness and skill of the attendant surgeon. For example, the proximal pin connectors are placed in a rubber surgical glove during the surgical procedure and before insertion into the heart pulse generator.

SUMMARY OF THE INVENTION

It is therefore an object of the present invention to prevent extraneous energies from being applied to the proximal connector of a heart pacemaker lead, with the resultant micro-shock hazard to the patient's heart.

In accordance with this and other objects of the invention, there is provided an antishock, insulated male-type connector adapted to be coupled to a heart pulse generator, comprising an electrical conductor, an electrically conductive pin and a layer of insulating material disposed about the electrical lead and pin with only a controlled portion of the pin not covered thereby. Further, an electrically conductive element is disposed upon the surface of the insulating material in a manner such that upon insertion into a female-type receptacle associated with its heart pulse generator, the electrically conductive element is brought into contact with the the pin, whereby a circuit is only then completed between heart pulse generator and the distal electrode coupled to the patient's heart.

The female-type receptacle associated with the heart pulse generator comprises at least two jaws, one of which is movable upon insertion of the aforedescribed connector to press the electrically conductive element into contact with the electrically conductive pin.

In one illustrative embodiment of this invention, the electrically conductive element takes the form of a ring disposed axially with respect to the electrically conductive pin and separated therefrom by an insulating, elastic material, which is compressed to permit at least a portion of the ring to come into electrical contact with the pin.

In a further embodiment of this invention, the electrically conductive element may take the form of a reed element having a first end secured with respect to the insulating layer and a second end remote therefrom free to permit flexing of the reed element into contact with the electrically conductive pin.

BRIEF DESCRIPTION OF THE DRAWINGS

These and other objects and advantages of the present invention will become more apparent by referring to the following detailed description and accompanying drawings, in which:

FIGS. 2A and 2B, 3, 4A and 4B, 5A and 5B, 6 and 7 are cross-sectioned views, partially broken away, of various other embodiments of this invention; and FIG. 8 is a simplified plan view of the female connector mechanism for receiving and applying pressure to the antishock, insulated connector of this invention.

FIGS. 9A and 9B are perspective views, respectively, of a cardiac external pulse generator including the female receptacles for receiving the male-type connectors of this invention, and of the mechanism for receiving and selectively applying pressure to the antishock, insulated connector of this invention.

DESCRIPTION OF THE PREFERRED EMBODIMENTS

Figure 1:
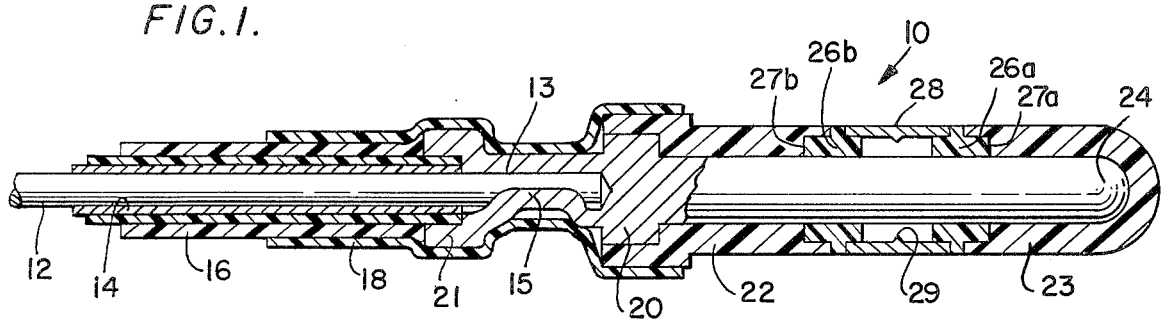
FIG. 1 is a sectioned view, partially broken away, of the antishock, insulated connector in accordance with the teachings of this invention.

With regard to the drawings and in particular to FIG. 1, there is shown an antishock, insulated, male-type connector 10 in accordance with teachings of this invention and adapted to be coupled with a cardiac pulse generator. In particular, the connector 10 includes an electrical conductor 12 with a suitable layer 14 of insulating material disposed thereabout. A portion of the insulating layer 14 is removed to provide an exposed portion 13 of the electrical conductor 12 for making electrical contact with an electrically conductive, male-type pin 24. In particular, the pin 24 has integrally formed therewith ferrules 20 and 21 each having an opening therein for receiving and electrically coupled with the exposed portion 13 of the electrical conductor 12. Second and third insulating layers 22 and 23 are disposed about the pin 24, and further, a fourth layer 18 of a suitable insulating material is disposed about the ferrules 20 and 21, overlapping insulating layers 14 and 16. A crimp 15 is placed between the ferrules 20 and 21, whereby the pin 24 is electrically coupled to the electrical conductor 12. In an illustrative embodiment of this invention, the layer 18 of insulating material is a polyolefin and is heat shrunk about the ferrules 20 and 21, and the insulating layers 16 and 22 whereby a fluid-tight seal is formed therewith. The insulating layer 16 is polyolefin and is heat shrunk about layer 14. In such an embodiment of this invention, the layers 22 and 23 may be made of a suitable insulating material such as Valox, as manufactured by General Electric. The conductor 12 may be made of a suitable electrical material such as stainless steel, and the pin 24 may be made of a suitable electrically conductive material such as a phosphorus bronze with a gold plate flashed thereon.

As shown in FIG. 1, a flexible, annularly-shaped element 28 made of a suitable electrically conductive material such as a gold-plated phosphorus bronze, is disposed axially about the pin 24 with its exterior surface flush with that of the insulating layers 22 and 23. The element 28 includes at least one raised portion 29 on its inner surface, whereby when pressure is applied to the annularly-shaped element 28, the raised portion 29 is brought into contact with the pin 24. Further, a pair of annular grooves 27a and 27b are disposed respectively within the interior surface of the insulated layers 22 and 23, whereby a pair of annularly-shaped spacer members 26a and 26b may be disposed therein axially about the pin 24. As shown in FIG. 1, the spacer members 26a and 26b overlap the edges of the annularly-shaped element 28, respectively, and serve to seal out all ambient fluid from the area between the element 28 and the pin 24. As seen in FIG. 1, the spacers 26a and 26b form a space between the pin 24 and the annularly-shaped element 28. Illustratively, an insulating gap is formed between the pin 24 and the element 28, having a dimension as measured along a radius extending from the axis of the pin 24, in the range of 0.007 to 0.012 inches. This gap provides sufficient insulating space to prevent microshocks from being applied thereacross and through the pin 24 and the electrical conductor 12 to the patient's heart.

Referring now to FIG. 8, there is shown in simplified fashion the manner in which the antishock insulating connector 10 is coupled to a device 40 such as a cardiac pulse generator in particular, the male-type connector 10 is inserted within a female type receptacle 50 of the cardiac pulse gnerator 40. In one illustrative embodiment of this invention, the pulse generator may take the form of an external pulse generator manufactured under the designation of No. 5375 by Medtronic, Inc. As illustrated in simplified fashion, a plurality of jaws 42, 44 and 46 serve to grasp and to retain the connector 10. As more fully shown in FIG. 9B, the jaws 42 and 44 take the form of support members having openings 51a and 51b for receiving the connector 10. In particular, at least one of the jaws, e.g. jaw 46 as shown in FIG. 8, is movably disposed from a first, receiving position wherein the connector 10 may be readily inserted within the receptable 50 to a second, retaining position, wherein the jaw 46 exerts pressure upon the annularly-shaped element 28. Upon insertion of the connector pin 10 within the receptacle 50, jaw 46 is brought into contact with the element 28 and sufficient pressure is exerted upon the annularly-shaped element 28, whereby it is offset sufficiently that the raised portion 29 is brought into contact with the pin 24. Thus, when the element is in its unflexed condition, the pin 24 and its coupled electrical conductor 12 remain insulated from the surrounding environment whereby possible micro-watt shocks are prevented from being applied along the conductor 12 to the patient's heart. Further, only when the connector 10 is inserted within the receptacle 50 of the cardiac pulse generator 40, is there a circuit completed between the annularly-shaped element 28 and the pin 24, whereby a suitable signal may be applied as through the jaw 46, the annular element 28, the pin 24 and the conductor 12 to the patient's heart.

Figure 2A:
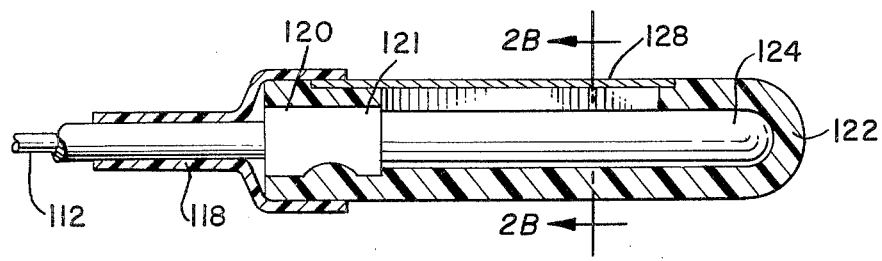
Figure 2B:
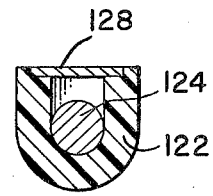

Referring now to FIGS. 2A and 2B, there is shown a further embodiment of this invention, wherein the electrically conductive element taking the form of a metallic reed 128, is mounted at one end with a mid-portion thereof to be depressed whereby electrical contact is made between the element 128 and an electrically conductive pin 124. In a manner similar to that described above, a male-type connector 100 comprises an insulated electrical conductor 112, having a ferrule 120 securing the conductor 112 to the pin 124. A layer 122 of a suitable material is disposed about the pin 124 and has a U-shaped cross-section as shown in FIG. 2B. Further, a second insulating layer 118 is disposed about and overlaps the insulating layer 122 and the electrical conductor 112. When pressure is applied to the metallic reed 128, its middle portion is flexed into contact with pin 124, whereby a circuit is completed between the cardiac pulse generator and the patient's heart through the element 123, the pin 124 and the connector 112. It is contemplated that connector 100 would be inserted into a cardiac pulse generator as described above, but would require orientation therein to align the reed 123 with the movable jaw. Such orientation may be provided by the "dee" shape of the connector 100 relative to a similar shape in the female connector formed within a pulse generator (not shown).

Figure 3:
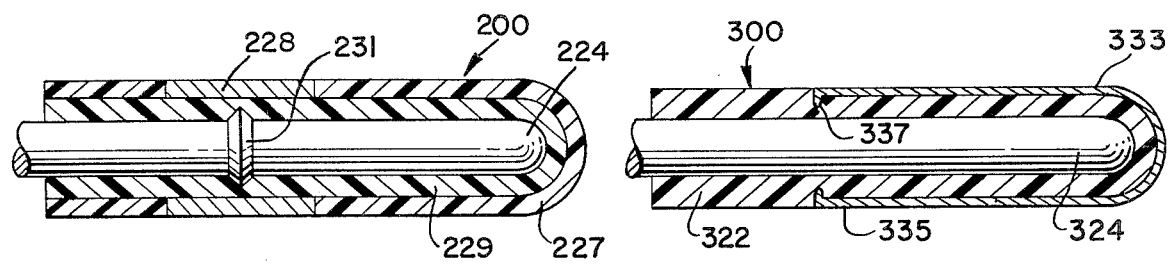

In FIG. 3, there is shown an embodiment of this invention, in which a male-type connector 200 includes a pin 224 and is covered successively with layers 229 and 227. Further, a pointed, annularly-shaped raised portion 231 is disposed about the electrical pin 224 and in alignment with an annularly-shaped, electrically conductive element 228 disposed thereabout. The first layer 229 of insulating material is of a relatively soft elastomeric material such as urathane or silicone, whereby upon exertion of pressure radially against the electrically conductive element 228, the pointed, raised portion 231 may readily penetrate or puncture the layer 229, whereby contact is made with the raised portion 231 and the annularly-shaped element 228. Further, the second, external layer 227 is made of a relatively harder insulating material such as the plastic manufactured under the name, Valox, by General Electric. The embodiment of FIG. 3 is particularly effective in preventing a discharge between the element 228 and the raised portion 231, due to the insertion of the insulating layer 229 therebetween and the geometric shape of element 228.

Figure 4A:
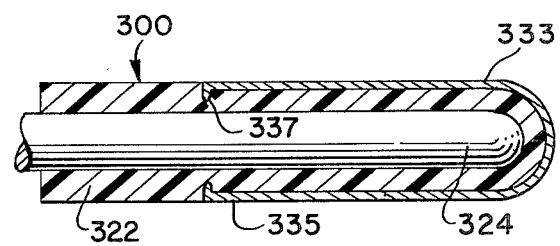
Figure 4B:
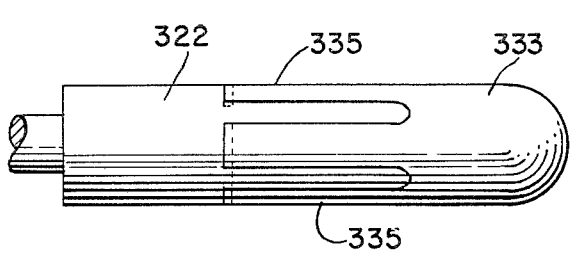

Referring now to FIGS. 4A and 4B, there is shown a still further embodiment of this invention in which a male-type connector 300 comprises a metallic pin 324 covered with an insulating layer 322 made of a suitable insulating material such as one of the elastomers urathane or silicone. Further, a sheath or collar 322 of electrically conductive material is disposed about the leading portion of the connector 300 and includes, as shown more clearly in FIG. 4B, a plurality of fingers 335 extending substantially parallel with respect to the axis of the pin 324. As more clearly shown in FIG. 4A, each of the fingers 335 includes at its free end, a tip contact 337 having a relatively sharp point thereon, whereby when pressure is applied to one of the fingers 335 in the manner as described above, the tip 337 is permitted to pierce or penetrate through the insulating layer 322 and contact the electrically conductive pin 324.

Figure 5A:
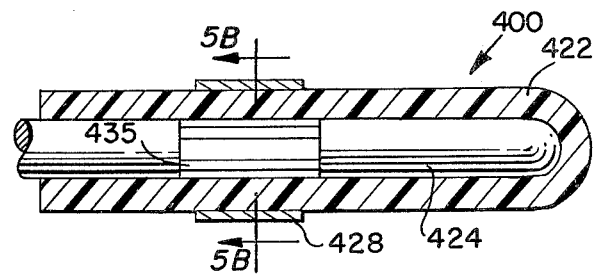
Figure 5B:
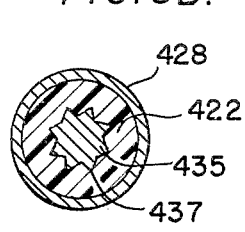

In FIGS. 5A and 5B, there is shown a further, illustrative embodiment of this invention taking the form of a male-type connector 400 comprising an electrically conductive pin 424 covered by an insulating layer 422 made of a suitable elastomer material, and an annularly-shaped metallic, electrically conductive element 428 disposed upon the surface of the insulating layer 422. As shown more clearly in FIG. 5B, a plurality of splines 435 is disposed evenly about the circumference of a limited portion of the pin 424, each having a point 437 for penetrating or piercing the insulating layer 422. More particularly, when pressure is applied radially against the exposed surface of the electrically conductive element 428, the layer of insulating material 422 is pressed against the relatively sharp points 437 of the splines 435, whereby at least one of the splines 435 is brought into contact with the element 428 and a circuit is completed through the element 428, the splines 435 and the electrically conductive pin 424.

Figure 6:
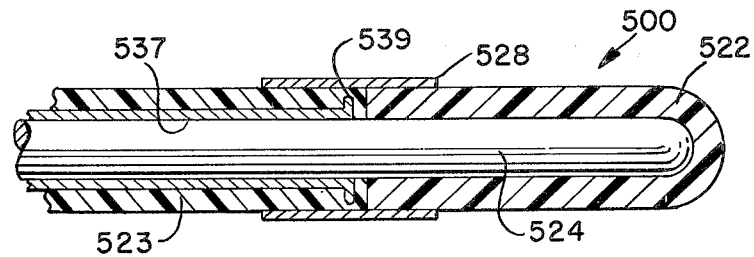

As shown in FIG. 6, a still further embodiment of this invention, a male-type connector 500, comprises an electrically conductive pin 524 covered with layers 522 and 523 of an elastimer insulating material, and an annularly-shaped element 528 made of a suitable electrically conductive material and disposed about the insulating layers 522 and 523, and the metallic pin 524. Further, a tube or sleeve 537 made of a suitable electrically conductive material is disposed about the pin 524, intermediate the pin 524 and the insulating layer 523. The leading end of the tube 537 is formed to provide a flared, flange-like member 539 having a sharp edge thereon. When axially-directed pressure is applied to the annularly-shaped element 528, the flange-like member 539 penetrates or pierces the insulating layer 523, whereby it is brought into contact with the element 528 and a circuit is completed therebetween to its electrical conductor (not shown).

Referring now to FIG. 7, there is shown a still further embodiment of this invention in the form of a male-type connector 600 comprising a metallic pin 624 with a knurl 627 to which a layer 622 of a suitable insulating material such as Valox is ultrasonically welded. The knurl 627 is used to increase the mechanical pullout strength of the pin 624 relative to the insulating layer 622. Further, an electrically conductive, annularly-shaped element 628 is disposed substantially concentric with respect to the axis of the pin 624 in a manner to be more fully explained. In particular, annularly-shaped grooves 642a and 642b are formed as shown in FIG. 7 within that portion of the insulating layer 622 adjacent the metallic pin 624, whereby there is formed a cavity by the insulating layer 622 and the annularly-shaped element 624 into which may be injected a relatively elastic, insulating material. The injected insulating material forms a layer 639 thereof disposed between the pin 624 and the annnularly-shaped element 628 of sufficient spacing to prevent an inadvertent discharge thereacross. In an alternative mode of manufacture, the relatively soft insulating material 639 is molded as a sleeve within element 628. Next, the insulator 618 and molded sleeve 639 are assembled on pin 624 and thereafter, the leading portion of the pin 624 is inserted within the layer 622 of insulating material formed as a cup. The connector 600 is coupled to a mechanical transducer which ultrasonically vibrates the pin 624 as it is being inserted into layer 622. The interface between the pin 624 and the layer 622 is heated by the vibration, thus causing the layer 622 to experience localized melting and to be welded to the pin 624. In operation, as explained above, pressure is applied radially against the exposed surface of the annularly-shaped element 628, whereby the element 628 is compressed toward the pin 624 through the insulating material 639, whereby contact is made therebetween.

In FIGS. 9A and 9B, there is shown the details of the receptacle 50 for receiving the antishock, insulating connector 10 of this invention. Referring first to FIG. 9A, the device 40 includes first and second receptacles or openings 50a and 50b, each for receiving a connector 10. It is apparent that the two such connectors 10 may be formed as in a single, molded connector assembly, with each connector 10 being aligned with a receptacle 50. In use, the operator grasps the cardiac pulse generator 40, depressing each of a pair of buttons 52a and 52b toward each other, whereby the aforementioned buttons slide over the elements 54a and 54b, respectively, to permit the withdrawal of at least one of the jaws, e.g. jaw 46, as explained above, with regard to FIG. 8. Further details of the operating mechanism for withdrawing the one jaw 46 are shown in FIG. 9B. In particular, the button 52a includes a thrust member 56 protruding to engage a cam 58; in particular, the thrust member 56 is threadably fastened to opening 60 of cam 58. The cam 58 is slideably restrained in a housing (not shown) of the cardiac pulse generator 40 and as is evident in FIG. 9B, follows the motion of the pushbutton 52a. The inner housing of the cardiac pulse generator 40 further includes the pair of support members or jaws 42 and 44 between which is disposed an essentially L-shaped cam follower member 62 which contains jaw 46 pivotally supported therebetween by a pin 66 disposed through openings within the members 42 and 44; in particular, an opening 72 is shown in FIG. 9B within member 44, while the other similar opening is hidden in this figure. Integrally formed with the cam follower member 62 is an arm 64 that is biased by a suitable spring member (not shown) into contact with the cam 58 so as to follow its motion. In particular, a spiral-shaped spring may be disposed about the pin 66 having one end secured to support members 42 or 44 and the other end secured to the cam follower member 62, whereby the clamping force exerted on the connector 10 is made independent of the pressure applied by the attending physician to either of the buttons 52a or 52b. Further, the movable jaw 46 having a jaw surface of a length corresponding to the axial length of the element 28, is formed as a part of the follower member 62 and is not shown in FIG. 9B.

As shown in FIG. 9B, the connector 10 of this invention is inserted within the receptacle opening 50a, where it is held by a plurality of jaws, as more fully shown in FIG. 8. In one embodiment of this invention, the operator presses the pushbutton 52a thereby directing the cam 58 to the right and rotating the cam follower member 62 in a counterclockwise direction, as seen in FIG. 9B, whereby at least one jaw, e.g. jaw 46 as shown in FIG. 8, is retracted from the opening 50a. Upon insertion of the connector 10 into the openings 51a and 51b, the pushbutton 52a is released, whereby the biasing motion of the spring associated with the cam followers 62 rotates the cam follower 62 in a clockwise direction, as shown in FIG. 9B, whereby the one jaw 46 as a part of member 62 is brought into contact with the connector 10, to exert a pressure along a radial direction with respect to the pin axis. Thus, the contact element is pressed against the pin, completing a circuit from the cardiac pulse generator 40 through the contact element, the pin and electrical conductor to the distal electrode associated with the patient's heart.

Thus, there has been shown a highly reliable connector and receptacle mechanism for receiving the connector, whereby the micro-shock hazard associated with unprotected connectors for a cardiac lead is substantially eliminated. In particular, there is generally disclosed a connector associated with a lead having a relatively flexible element made of electrically conductive material adapted to be flexed from an insulated position toward an electrically conductive pin associated with the electrical conductor, whereby a circuit is completed therethrough between the pulse generator and the patient's heart. The lead and connector are covered, except for the aforementioned electrical element, with an insulating material. The insulating material and/or the spacing disposed between the element and the metallic pin is sufficient to prevent a micro-shock from being directed across the intervening space. Thus, the potential shock hazard of an unprotected connector as presented to the patient is eliminated in that the electrode coupled with the patient's heart and its associated electrical connector and distal connector, are substantially insulated from such a discharge, while the connector remains unconnected from the pulse generator.

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. An antishock electrical connector adapted for the environment of an animal body, comprising:
   a. a first electrically conductive member;
   b. an electrical conductor affixed to and electrically coupled to said first electrically conductive member;
   c. a layer of insulating material disposed about substantially the entire surface of said first electrically conductive member;
   d. a second electrically conductive member disposed over said insulating layer and adapted to make electrical contact with said first electrically conductive member; and
   e. means for disposing said second electrically conductive member in a spaced relationship with said first conductive member to prevent extraneous charges applied to said second electrically conductive member from passing thereacross to said first electrically conductive member, and for providing a liquid-tight seal between said insulating layer and said second electrically conductive member to prevent the entrance of liquid into the space between said first and second electrically conductive members, said means permitting disposition of said second electrically conductive member between a first, normal position wherein said first and second electrically conductive members are spaced from each other, and a second, flexed position wherein said first and second electrically conductive members are in electrical contact with each other, thus forming an electrical circuit from said first conductive member through said second conductive member to said conductor.

2. The antishock connector as claimed in claim 1, wherein said second electrically conductive member comprises an annularly-shaped member disposed about said first electrically conductive member.

3. The antishock connector as claimed in claim 2, wherein said second electrically conductive member comprises a raised portion disposed upon that surface facing said first electrically conductive member, whereby in said second position, said raised portion and said first electrically conductive member are brought into electrical contact.

4. The antishock connector as claimed in claim 1, wherein said second electrically conductive member comprises a reed-like member having a first portion fixed with respect to said insulating layer and a second, spaced portion free to be disposed between said first and said second positions.

5. The antishock connector as claimed in claim 2, wherein said annular member includes at least one finger extending substantially parallel with respect to said first electrically conductive member, whereby a free end of said finger may be flexed between said first and said second position.

6. The antishock connector as claimed in claim 1, wherein said insulating layer covers said first electrically conductive member and is disposed between said first and said second electrically conductive members, and one of said first and second electrically conductive members includes a raised portion having a relatively sharp point disposed thereon toward the other of said first and second electrically conductive members, whereby when pressure is radially applied to said second electrically conductive member, said relatively sharp point penetrates said insulating layer.

7. The antishock connector as claimed in claim 6, wherein there is included a plurality of said raised portions in the form of spline members disposed substantially parallel to an axis of said first electrically conductive member and disposed about the periphery thereof.

8. The antishock connector as claimed in claim 1, wherein there is further included a sleeve disposed about and in contact with said first electrically conductive member, said sleeve having a flared edge disposed toward said second electrically conductive member whereby when pressure is readily applied to said second electrically conductive member, said second electrically conductive member is brought into contact with said flange.

9. The antishock connector as claimed in claim 1, wherein said insulating layer has an opening therein, said second electrically conductive member comprising an annularly-shaped member disposed about said first electrically conductive member and forming with said first electrically conductive member and the walls of said insulating layer a space therebetween, said space being filled with a second insulating layer having an elastic quality greater than that of said first-mentioned insulating layer, said first layer being made of an insulating material of a relatively inelastic material.

10. The antishock connector as claimed in claim 1, wherein said insulating layer has an opening therein, and said second electrically conductive member is disposed to cover at least a portion of said opening and forms a space with the side walls of said opening and said first electrically conductive member, said first electrically conductive member in its first position being spaced from said second electrically conductive member.

11. An antishock connector assembly comprising:
 a. a male-type pin adapted for the environment of an animal body, having:
  1. first and second electrically conductive members,
  2. an electrical conductor affixed to and coupled to said first electrically conductive member,
  3. a layer of insulating material disposed about substantially the entire surface of said first electrically conductive member,
  4. means for disposing said second electrically conductive member in a spaced relationship with said first conductive member and for providing a liquid-tight seal between said insulating layer and said second electrically conductive member to prevent the entrance of liquid into the space between said first and second electrically conductive members;
  5. said second electrically conductive member being flexible to permit movement between a first position wherein said second electrically conductive member is spaced from said first electrically conductive member, and a second position wherein said first and second electrically conductive members are in electrical contact with each other to establish a circuit through said first and second electrically conductive members and said electrical connector; and
 b. a female-type receptacle for receiving said male-type pin, including means operative to exert a radial force upon said second, flexible electrically conductive member when inserted therein, whereby said second electrically conductive member is disposed to its second position, thus forming said circuit.

12. The electrical connector assembly as claimed in claim 11, wherein said receptacle comprises a plurality of jaw-like members oppositely disposed to releasably grasp said male-type pin, at least one of said jaw-like members being movable from a first engaging position wherein said one jaw-like member exerts a force against said inserted pin, to a second position free of said pin whereby said pin may be removed from said receptacle.

* * * * *